(12) United States Patent
Aqad et al.

(10) Patent No.: US 9,880,469 B2
(45) Date of Patent: Jan. 30, 2018

(54) RESINS FOR UNDERLAYERS

(71) Applicants: Rohm and Haas Electronic Materials LLC, Marlborough, MA (US); Rohm and Haas Electronic Materials Korea Ltd., Cheonan (KR)

(72) Inventors: Emad Aqad, Northborough, MA (US); Mingqi Li, Shrewsbury, MA (US); Shintaro Yamada, Shrewsbury, MA (US); Sung Wook Cho, Gyeonggi-do (KR)

(73) Assignees: Rohm and Haas Electronic Materials LLC, Marlborough, MA (US); Rohm and Haas Electronic Materials Korea Ltd, Seoul (KR)

( * ) Notice: Subject to any disclaimer, the term of this patent is extended or adjusted under 35 U.S.C. 154(b) by 0 days.

(21) Appl. No.: 14/792,968

(22) Filed: Jul. 7, 2015

(65) Prior Publication Data

US 2016/0016872 A1    Jan. 21, 2016

Related U.S. Application Data

(60) Provisional application No. 62/024,938, filed on Jul. 15, 2014.

(51) Int. Cl.
| | | |
|---|---|---|
| *G03F 7/09* | (2006.01) |
| *G03F 7/36* | (2006.01) |
| *G03F 7/30* | (2006.01) |
| *C07C 39/17* | (2006.01) |
| *C07C 39/14* | (2006.01) |
| *C07D 213/16* | (2006.01) |
| *C08G 8/04* | (2006.01) |
| *C08G 8/10* | (2006.01) |
| *C08G 12/34* | (2006.01) |
| *C08G 12/26* | (2006.01) |
| *C08G 12/08* | (2006.01) |
| *C09D 161/06* | (2006.01) |
| *C09D 161/22* | (2006.01) |
| *C08G 8/08* | (2006.01) |

(52) U.S. Cl.
CPC ............. *G03F 7/094* (2013.01); *C07C 39/14* (2013.01); *C07C 39/17* (2013.01); *C07D 213/16* (2013.01); *C08G 8/04* (2013.01); *C08G 8/08* (2013.01); *C09D 161/06* (2013.01); *G03F 7/091* (2013.01); *G03F 7/30* (2013.01); *G03F 7/36* (2013.01); *C07C 2603/18* (2017.05); *C07C 2603/24* (2017.05); *C07C 2603/40* (2017.05); *C07C 2603/42* (2017.05); *C07C 2603/50* (2017.05); *C07C 2603/52* (2017.05)

(58) Field of Classification Search
None
See application file for complete search history.

(56) References Cited

U.S. PATENT DOCUMENTS

| | | | |
|---|---|---|---|
| 7,303,855 B2 | 12/2007 | Hatakeyama et al. | |
| 7,378,217 B2 | 5/2008 | Oh et al. | |
| 7,862,990 B2 | 1/2011 | Yoon et al. | |
| 2002/0132134 A1* | 9/2002 | Hu | C07C 13/567 428/690 |
| 2006/0269867 A1 | 11/2006 | Uh et al. | |
| 2007/0275325 A1 | 11/2007 | Hatakeyama et al. | |
| 2008/0153033 A1 | 6/2008 | Hyung et al. | |
| 2010/0021830 A1 | 1/2010 | Kim et al. | |
| 2010/0099044 A1* | 4/2010 | Hatakeyama | G03F 7/095 430/285.1 |
| 2012/0045900 A1* | 2/2012 | Watanabe | C07C 69/753 438/703 |
| 2012/0171611 A1 | 7/2012 | Ideno et al. | |
| 2013/0189533 A1 | 7/2013 | Okuyama et al. | |

FOREIGN PATENT DOCUMENTS

| | | | |
|---|---|---|---|
| CN | 102675128 A | * | 9/2012 |
| DE | 10 2004 020 046 A1 | * | 7/2005 |
| JP | 03014815 A | | 1/1991 |
| JP | 2005-114921 | * | 4/2005 |
| JP | 2006285075 A | | 10/2006 |
| JP | 2009013096 A | | 1/2009 |
| JP | 2010271654 A1 | | 12/2010 |
| JP | 2013170171 A | | 2/2013 |
| KR | 10-2010-0080148 | * | 7/2010 |
| KR | 20100080148 A | | 7/2010 |
| KR | 2013039864 A | | 4/2013 |

OTHER PUBLICATIONS

Machine-assisted English translation for JP 2005-114921 as provided by JPO (2005).*
English abstract for KR 10-2010-0080148 (2010).*
Chemical Abstract (Accession No. 2005:673666)—chemical abstract for DE 10 2004 020 046 A1 (2005).*
Derwent Abstract(Derwent-Acc-No. 2012-Q51536)—English abstract for CN 102675128 A (2012).*
Krohn et al ("Transition Metal Catalyzed Oxidations; 4. Improved Method for the Oxidation of 1- and 2-Naphthols to 1,2-Naphtoquinones", Synthesis (1990), (12), p. 1141-3).*
Search report for corresponding Taiwan Application No. 104122505 dated Jun. 17, 2016.
Search report for corresponding China Application No. 201510411991.7 dated Feb. 22, 2017.

* cited by examiner

*Primary Examiner* — Sin Lee
(74) *Attorney, Agent, or Firm* — S. Matthew Cairns

(57) ABSTRACT

Polymeric reaction products of certain substituted tetraarylmethane monomers are useful as underlayers in semiconductor manufacturing processes.

19 Claims, No Drawings

RESINS FOR UNDERLAYERS

The present invention relates generally to field of manufacturing electronic devices, and more specifically to the field of materials for use in semiconductor manufacture.

It is well-known in lithographic processes that a resist pattern can collapse due to surface tension from the developer used if the resist pattern is too tall (high aspect ratio). Multilayer resist processes (such as three- and four-layer processes) have been devised which can address this issue of pattern collapse where a high aspect ratio is desired. Such multilayer processes use a resist top layer, one or more middle layers, and a bottom layer (or underlayer). In such multilayer resist processes, the top photoresist layer is imaged and developed in typical fashion to provide a resist pattern. The pattern is then transferred to the one or more middle layers, typically by etching. Each middle layer is selected such that a different etch process is used, such as different plasma etches. Finally, the pattern is transferred to the underlayer, typically by etching, such as reactive ion etch (RIE). Such middle layers may be composed of various materials while the underlayer materials are typically composed of high carbon content materials. The underlayer material is selected to provide desired antireflective properties, planarizing properties, as well as etch selectivity.

As aspect ratios of the patterned high carbon content materials increase and feature sizes decrease, pattern transfer from the high carbon content underlayer materials to the substrate by fluorine-containing RIE induces severe pattern deformation ("wiggling") in the underlayer material, which ultimately prevents successful pattern transfer into the substrate. Another important parameter that affects etch selectivity is the Ohnishi Number (ON), which is the total number of atoms in a molecule ($N_T$) divided by the number of carbon atoms ($N_C$) minus the number of oxygen atoms ($N_O$) in the molecule, or $N_T/(N_C-N_O)$. The ON is proportional to a material's etch response, with smaller ONs indicating better etch selectivity.

Various attempts have been made to develop underlayer materials which possess desired antireflective properties and etch selectivity, and which are suitable for use with these multilayer processes. A number of these attempts involve the use of 9,9-diaryl-9H-fluorene monomers, where each of the aryl moieties has a group, such as a hydroxy or aryloxy substituent, that activates the aryl moiety toward subsequent polymerization. For example, U.S. Published Pat. App. No. 2008/0153033 discloses polymers having a 9,9-bis(substituted phenyl)fluorene repeat unit of the formula

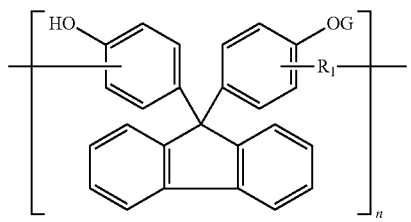

wherein G is an aromatic ring-containing group having an alkoxy group, and $R_1$ is a methylene or includes a non-fluorene-containing aryl linking group. Such aromatic polymers do not show desired etch selectivity, that is, etch resistance. There remains a need for underlayer materials that possess desired antireflective properties and improved etch selectivity, particularly improved etch resistance to $O_2$ and $CF_4$ plasmas.

The present invention provides new high carbon-content materials based on tetraaryl methane monomers, where only one of the aryl moieties has an activating group. These materials possess key chemical and physical properties such as: high thermal stability, high carbon content, low H content, high modulus, and high film density. The latter properties are critical for overcoming etch selectivity issues and to prevent pattern deformation. The present materials have reduced oxygen content compared to conventional fluorene-based materials and, therefore, have a smaller ON as compared to conventional materials, and correspondingly better etch selectivity.

The present invention provides a polymeric reaction product comprising polymerized units of one or more tetraaryl monomers of formula (1)

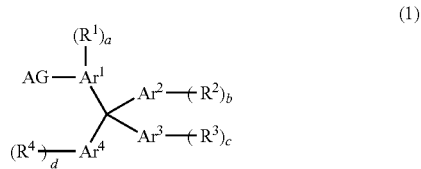

wherein AG represents an activating group chosen from OR, $NR_2$, and SR; $Ar^1$, $Ar^2$, $Ar^3$ and $Ar^4$ independently represent an aryl moiety; R is independently chosen from H, an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; $R^1$, $R^2$, $R^3$, and $R^4$ are independently chosen from an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; any 2 of $Ar^1$, $Ar^2$, $Ar^3$ and $Ar^4$ may be taken together along with the carbon to which they are attached to form a 5 or 6-membered fused alicyclic ring; a is an integer from 0 to 4; and b, c, and d are independently integers from 0 to 5.

Also provided by the present invention is a composition comprising the polymeric reaction product described above, an organic solvent, and optionally one or more additives chosen from curing agents and surfactants.

Further, the present invention provides a method of forming a patterned layer comprising disposing a layer of the composition described above on a substrate; removing the organic solvent to form a polymeric underlayer; disposing a layer of a photoresist on the polymeric underlayer; exposing the photoresist layer to actinic radiation through a mask; developing the exposed photoresist layer to form a resist pattern; and transferring the pattern to the polymeric underlayer to expose portions of the substrate.

The present invention even further provides tetraaryl methane monomers having the formula (1)

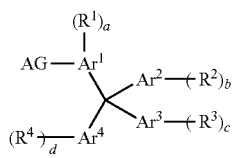
(1)

wherein AG represents an activating group chosen from OR, NR$_2$, and SR; Ar$^1$, Ar$^2$, Ar$^3$ and Ar$^4$ independently represent an aryl moiety; R is independently chosen from H, an optionally substituted C$_{1-30}$ alkyl, an optionally substituted C$_{2-30}$ alkenyl moiety, an optionally substituted C$_{2-30}$ alkynyl moiety, an optionally substituted C$_{7-30}$ aralkyl moiety, or an optionally substituted C$_{6-20}$ aryl moiety; R$^1$, R$^2$, R$^3$, and R$^4$ are independently chosen from an optionally substituted C$_{1-30}$ alkyl, an optionally substituted C$_{2-30}$ alkenyl moiety, an optionally substituted C$_{2-30}$ alkynyl moiety, an optionally substituted C$_{7-30}$ aralkyl moiety, or an optionally substituted C$_{6-20}$ aryl moiety; any 2 of Ar$^1$, Ar$^2$, Ar$^3$ and Ar$^4$ may be taken together along with the carbon to which they are attached to form a 5 or 6-membered fused alicyclic ring; a is an integer from 0 to 4; and b, c, and d are independently integers from 0 to 5; wherein at least one of Ar$^1$, Ar$^2$, Ar$^3$ and Ar$^4$ is an aryl moiety having 2 or more fused aromatic rings when none of Ar$^1$, Ar$^2$, Ar$^3$ and Ar$^4$ are joined to form a 5 or 6-membered fused alicyclic ring.

As used herein, when an element is referred to as being "disposed on" another element, it can be directly disposed on the other element or intervening elements may be present therebetween. In contrast, when an element is referred to as being "directly disposed on" another element, there are no intervening elements present.

It will be understood that although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

As used throughout this specification, the following abbreviations shall have the following meanings, unless the context clearly indicates otherwise: ° C.=degree Celsius; mmol=millimole; g=gram; μm=micron=micrometer; nm=nanometer; Å=angstrom; L=liter; mL=milliliter; sec.=second; min.=minute; and hr.=hour. All amounts are percent by weight and all ratios are molar ratios, unless otherwise noted. All numerical ranges are inclusive and combinable in any order, except where it is clear that such numerical ranges are constrained to add up to 100%. The abbreviation "wt %" refers to percent by weight, based on the total weight of a referenced composition, unless otherwise noted.

As used throughout the specification, "feature" refers to the geometries on a substrate, and particularly on a semiconductor wafer. The term "alkyl" includes linear, branched and cyclic alkyl. Likewise, "alkenyl" refers to linear, branched and cyclic alkenyl, and "alkynyl" refers to linear and branched alkynyl. By the term "curing" it is meant any process, such as polymerization or condensation, that increases the molecular weight of a material or composition. "Curable" refers to any material capable of being cured (polymerized) under certain conditions. The term "oligomer" refers to dimers, trimers, tetramers and other relatively low molecular weight materials that are capable of further curing. "Alicyclic" refers to a non-aromatic carbocyclic ring which may be saturated or unsaturated. The articles "a", "an" and "the" refer to the singular and the plural.

Tetraaryl methane monomers useful in forming the present reaction products have 4 aromatic rings directly bonded to a central carbon (methane), wherein only 1 aromatic ring is substituted with an activating group. Tetraaryl methane monomers of the invention have the formula (1)

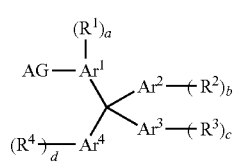
(1)

wherein AG represents an activating group chosen from OR, NR$_2$, and SR; Ar$^1$, Ar$^2$, Ar$^3$ and Ar$^4$ independently represent an aryl moiety; R is independently chosen from H, an optionally substituted C$_{1-30}$ alkyl, an optionally substituted C$_{2-30}$ alkenyl moiety, an optionally substituted C$_{2-30}$ alkynyl moiety, an optionally substituted C$_{7-30}$ aralkyl moiety, or an optionally substituted C$_{6-20}$ aryl moiety; R$^1$, R$^2$, R$^3$, and R$^4$ are independently chosen from an optionally substituted C$_{1-30}$ alkyl, an optionally substituted C$_{2-30}$ alkenyl moiety, an optionally substituted C$_{2-30}$ alkynyl moiety, an optionally substituted C$_{7-30}$ aralkyl moiety, or an optionally substituted C$_{6-20}$ aryl moiety; any 2 of Ar$^1$, Ar$^2$, Ar$^3$ and Ar$^4$ may be taken together along with the carbon to which they are attached to form a 5 or 6-membered fused alicyclic ring; a is an integer from 0 to 4; and b, c, and d are independently integers from 0 to 5. AG is preferably OR, and more preferably OH. R is preferably chosen from H, an optionally substituted C$_{1-20}$ alkyl, an optionally substituted C$_{2-20}$ alkenyl moiety, an optionally substituted C$_{2-20}$ alkynyl moiety, an optionally substituted C$_{7-20}$ aralkyl moiety, or an optionally substituted C$_{6-20}$ aryl moiety, more preferably chosen from H, an optionally substituted C$_{1-20}$ alkyl, an optionally substituted C$_{7-20}$ aralkyl moiety, or an optionally substituted C$_{6-20}$ aryl moiety, even more preferably chosen from H or an optionally substituted C$_{6-20}$ aryl moiety, and yet more preferably H. It is preferred that R$^1$, R$^2$, R$^3$, and R$^4$ are independently chosen from optionally substituted C$_{1-20}$ alkyl, optionally substituted C$_{2-20}$ alkenyl moiety, optionally substituted C$_{2-20}$ alkynyl moiety, optionally substituted C$_{7-30}$ aralkyl moiety, or optionally substituted C$_{6-20}$ aryl moiety, and more preferably optionally substituted C$_{1-20}$ alkyl, optionally substituted C$_{7-30}$ aralkyl moiety, or optionally substituted C$_{6-20}$ aryl moiety. It is preferred that a is 0 to 2, more preferably 0 or 1, and even more preferably 0. It is preferred that b, c, and d are independently an integer from 0 to 4, more preferably 0 to 2, and yet more preferably 0. A "substituted" alkyl, alkenyl, alkynyl, aralkyl, or aryl moiety refers to any alkyl, alkenyl, alkynyl, aralkyl, or aryl moiety having one or more of its hydrogens replaced with one or more substituents selected from C$_{1-20}$ alkyl, C$_{2-20}$ alkenyl, $C_{7-30}$ aralkyl, or $C_{6-20}$ aryl; and preferably from $C_{1-10}$ alkyl, $C_{2-12}$ alkenyl, $C_{7-30}$ aralkyl, or $C_{6-20}$ aryl.

In formula (1), $Ar^1$, $Ar^2$, $Ar^3$ and $Ar^4$ independently represent an aryl moiety. As used herein, "aryl moiety" refers to an aromatic ring system, which may be carbocyclic, heterocyclic, or a mixture thereof, and preferably is carbocyclic. The term "aryl moiety" includes: single aromatic rings such as phenyl or pyridyl; fused aromatic rings such as naphthyl, anthracenyl, phenanthrenyl, pyrenyl, or quinolinyl; and fused ring systems having both aromatic and alicyclic rings such as 1,2,3,4-tetrahydronaphthalene, 9,10-dihydroanthracene, or fluorene. A wide variety of aryl moieties may be used for each of $Ar^1$, $Ar^2$, $Ar^3$ and $Ar^4$, which may be unsubstituted or substituted. Such unsubstituted aryl moieties have from 5 to 40 carbons, preferably from 6 to 40 carbons, and more preferably from 6 to 35 carbons. It is preferred that $Ar^2$, $Ar^3$ and $Ar^4$ are independently chosen from optionally substituted $C_{6-40}$ aryl moieties, more preferably optionally substituted $C_{6-40}$ carbocyclic aryl moieties, and even more preferably unsubstituted $C_{6-30}$ carbocyclic aryl moieties. Suitable aryl moieties for $Ar^1$, $Ar^2$, $Ar^3$ and $Ar^4$ include, but are not limited to: phenyl, biphenyl, naphthalenyl, anthracenyl, phenanthrenyl, pyrenyl, tetracenyl, triphenylenyl, tetraphenyl, benzo[f]tetraphenyl, benzo[m]tetraphenyl, benzo[k]tetraphenyl, pentacenyl, perylenyl, benzo[a]pyrenyl, benzo[e]pyrenyl, benzo[ghi]perylenyl, coronenyl, quinolonyl, 7,8-benzoquinolinyl, fluorenyl, chrysenyl, triphenylenyl, and 12H-dibenzo[b,h]fluorenyl. Preferred aryl moieties include: phenyl, naphthalenyl, anthracenyl, phenanthrenyl, pyrenyl, tetracenyl, triphenylenyl, tetraphenyl, benzo[f]tetraphenyl, benzo[m]tetraphenyl, benzo[k]tetraphenyl, pentacenyl, perylenyl, benzo[a]pyrenyl, benzo[e]pyrenyl, benzo[ghi]perylenyl, coronenyl, and fluorenyl. It is more preferred that aryl moieties for $Ar^1$ are phenyl, naphthyl, anthracenyl, phenanthrenyl, pyrenyl, triphenylenyl, or perylenyl, and that aryl moieties for $Ar^2$, $Ar^3$ and $Ar^4$ are phenyl, naphthyl, anthracenyl, phenanthrenyl, pyrenyl, triphenylenyl, perylenyl, fluorenyl, benzo[b]fluorenyl, dibenzo[b,h]fluorenyl, benzo[de]anthracenyl, tetrahydroanthracenyl, or cyclopenta[def]phenanthrenyl. In $Ar^1$, the aromatic ring directly bonded to the central carbon of the monomer is substituted by an activating group, AG, which activates $Ar^1$ toward subsequent polymerization. Particularly preferred are tetraaryl methane monomers wherein any 2 of $Ar^1$, $Ar^2$, $Ar^3$ and $Ar^4$ are joined to form a fused 5 or 6-membered ring. When any 2 of $Ar^1$, $Ar^2$, $Ar^3$ and $Ar^4$ are joined to form a fused 5 or 6-membered ring, such fused ring system comprises from 3 to 6 fused rings, and preferably from 3 to 5 fused rings.

Preferred monomers of formula (1) where none of $Ar^1$, $Ar^2$, $Ar^3$ and $Ar^4$ are joined to form a fused ring include, without limitation, the following:

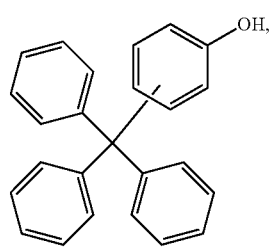

(1a)

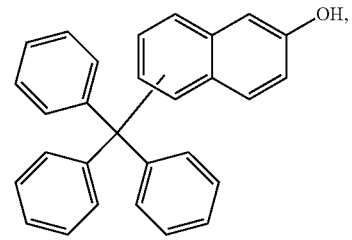

(1b)

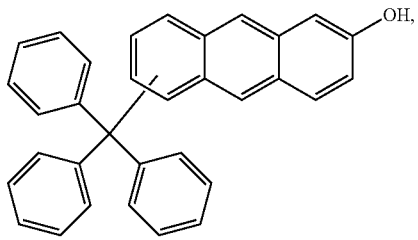

(1c)

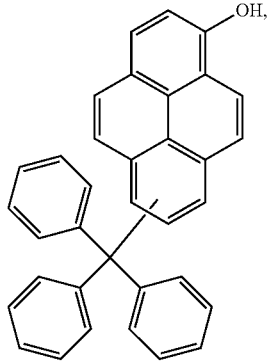

(1d)

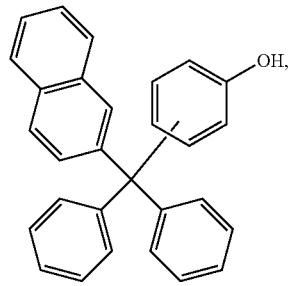

(1e)

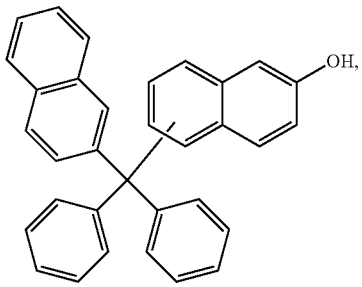

(1f)

-continued (1g) 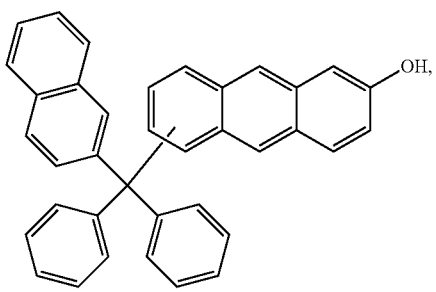

(1h) 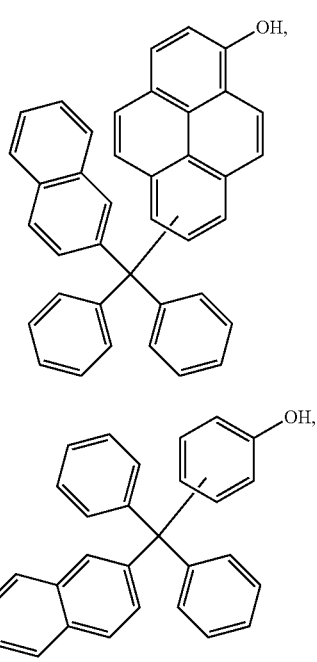

(1i)

(1j) 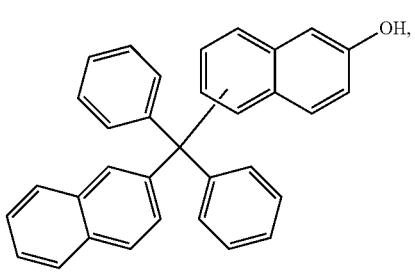

(1k) 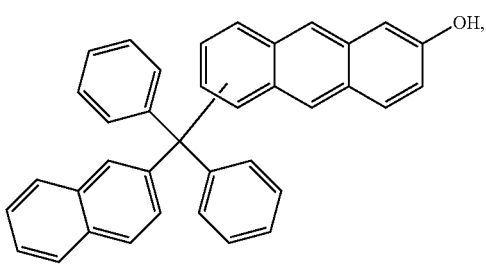

-continued (1l) 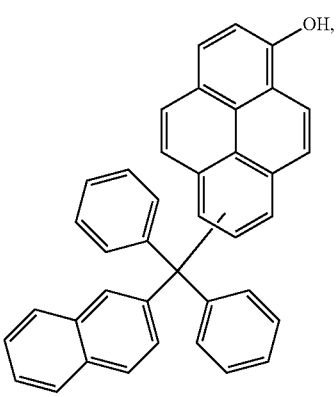

(1m) 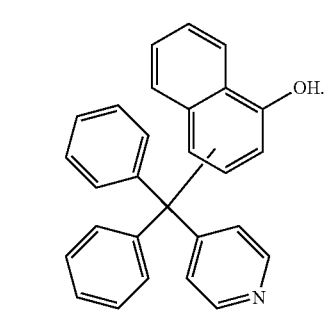

More preferred monomers of formula (1) where none of $Ar^1$, $Ar^2$, $Ar^3$ and $Ar^4$ are joined to form a fused ring are those wherein at least one of $Ar^1$, $Ar^2$, $Ar^3$ and $Ar^4$ is an aryl moiety having 2 or more fused aromatic rings or is a heteroaromatic moiety, even more preferred are those wherein at least one of $Ar^1$, $Ar^2$, $Ar^3$ and $Ar^4$ is an aryl moiety having 2 or more fused aromatic rings or at least one of $Ar^2$, $Ar^3$ and $Ar^4$ is a heteroaromatic moiety, and still more preferred are those wherein at least one of $Ar^1$, $Ar^2$, $Ar^3$ and $Ar^4$ is an aryl moiety having 2 or more fused aromatic rings.

Monomers of formula (1) wherein 2 of $Ar^1$, $Ar^2$, $Ar^3$ and $Ar^4$ are joined to form a fused 5 or 6-membered alicyclic ring have the general formula (1-1), (1-2) or (1-3):

(1-1) 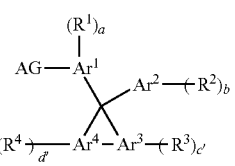

(1-2) 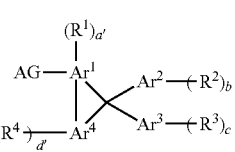

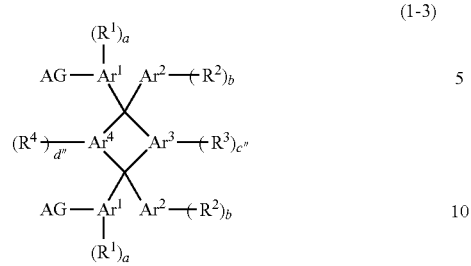
(1-3)

wherein AG, Ar¹, Ar², Ar³, Ar⁴, R¹, R², R³, R⁴, a, b, and c are as defined above; a' is an integer from 0 to 3; c' and d' are independently integers from 0 to 4; and c" and d" are independently integers from 0 to 4. Preferably, a' is an integer from 0 to 2, and more preferably a'=0 or 1, and still more preferably a'=0. It is preferred that c' is an integer from 0 to 3, more preferably 0 or 1, and even more preferably c'=0. It is preferred that d' is an integer from 0 to 3, more preferably 0 or 1, and even more preferably d'=0. Preferably, c" and d" are independently integers from 0 to 2, and more preferably 0 or 1. More preferably one of c" and d" is 0, and even more preferably both c" and d" are 0. It is preferred that monomers of formula (1) wherein 2 of Ar¹, Ar², Ar³ and Ar⁴ are joined to form a fused 5 or 6-membered alicyclic ring have the formula (1-1) or (1-3).

Preferred monomers of formulae (1-1) and (1-2) include, without limitation, the following:

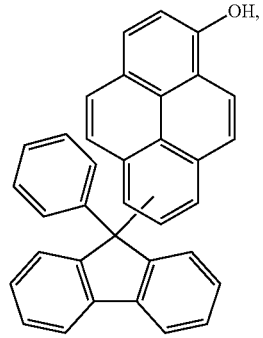
(1-1a)

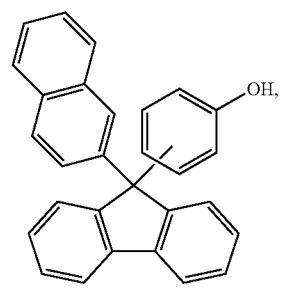
(1-1b)

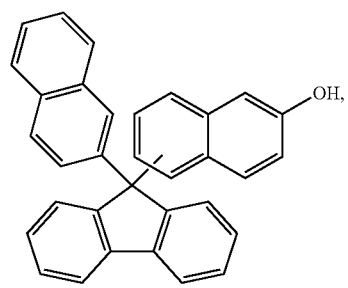
(1-1c)

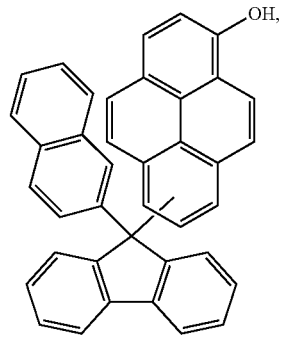
(1-1d)

(1-1e)

(1-1f)

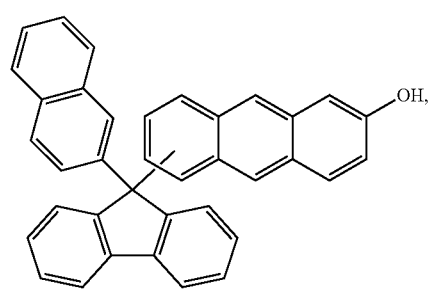
(1-1g)

(1-1h)

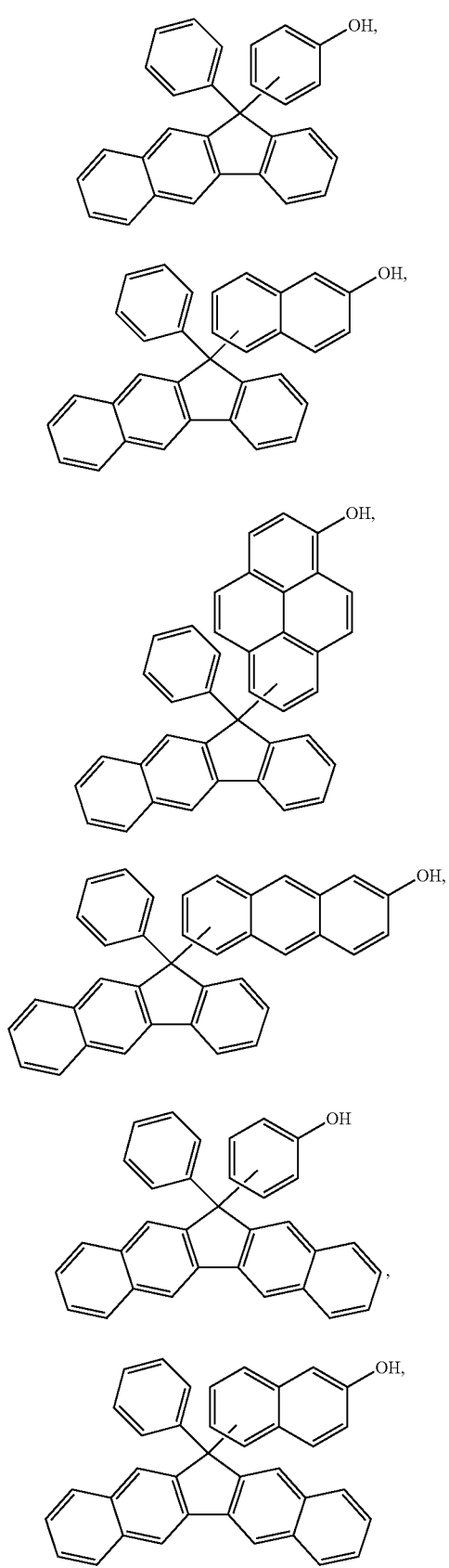
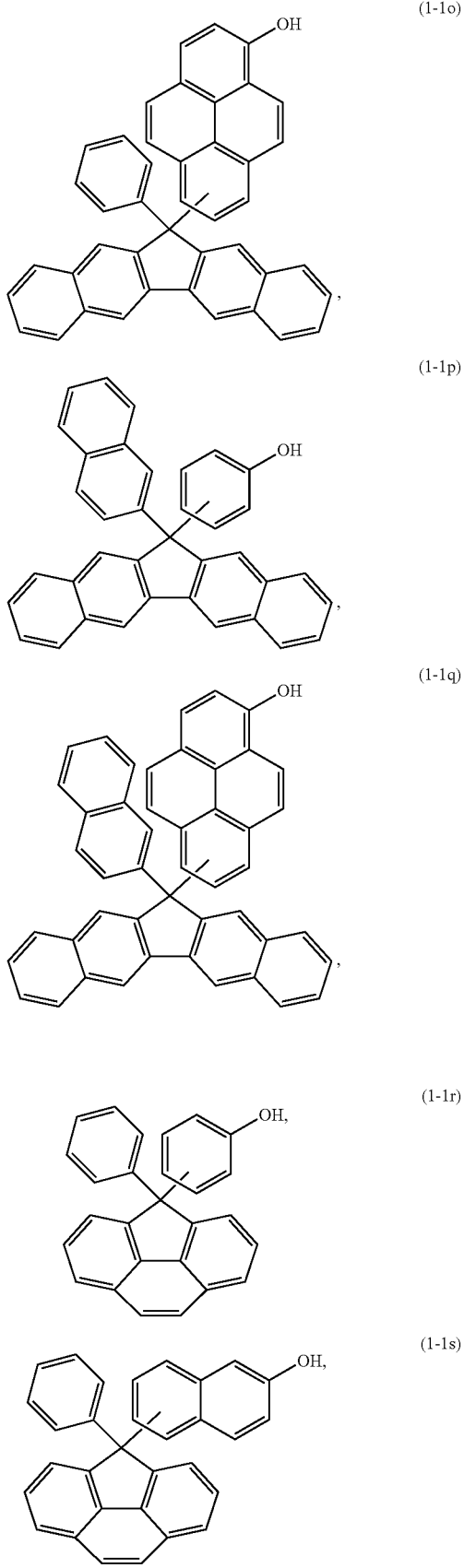

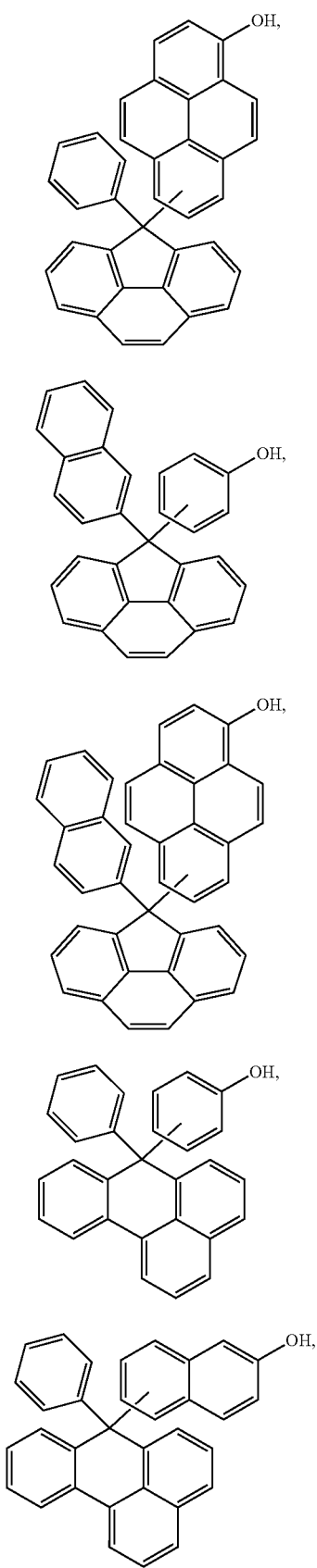
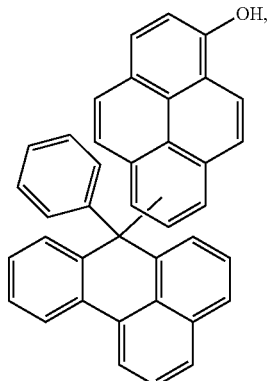
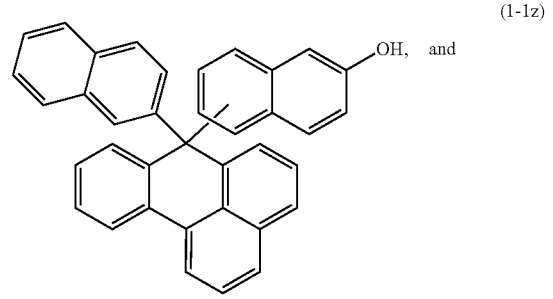
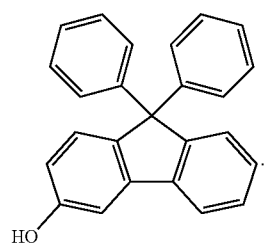
Preferred monomers of formula (1-3) include, without limitation, the following:
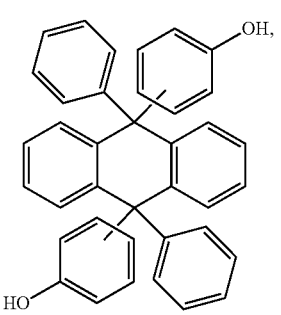

(1-3b)

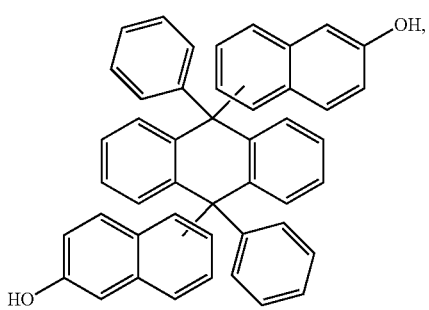

(1-3c)

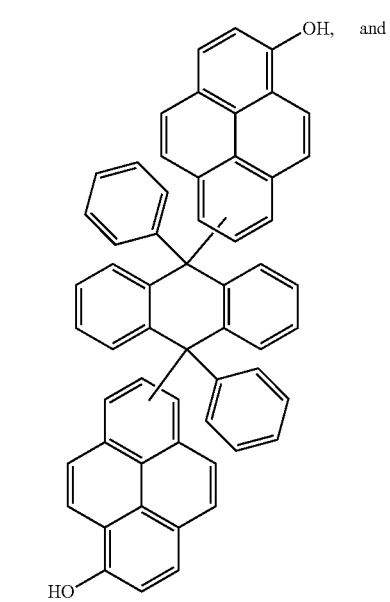 and (1-3d)

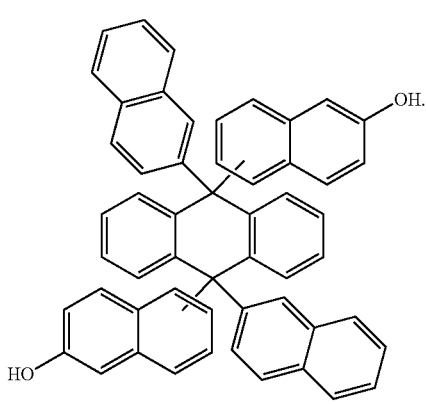

The monomers of the present invention can readily be prepared by methods known in the art. Typically, the present monomers may be prepared by first reacting a diaryl ketone, such as benzophenone or 9-fluorenone, with an aryl Grignard or aryl lithium reagent, such as phenylmagnesium bromide or phenyl lithium, in a suitable solvent to form a triaryl methanol intermediate. Next, the triaryl methanol intermediate is reacted with an aryl moiety containing an activating group, such as OH, in a suitable solvent in the presence of an acid catalyst such as p-toluenesulfonic acid (pTSA). Preferably slightly less than 1 equivalent of the aryl moiety containing an activating group is used in the reaction. A hydroxy, amino or mercapto-substituted diaryl ketone, such as 3-hydroxy-9-fluoreneone, may be used to prepare the present monomers of formula (1) provided that the hydroxyl, amino or mercapto group is first protected before reacting the compound with an aryl Grignard or aryl lithium reagent. Such protecting groups are well-known to those skilled in the art. For example, 3-hydroxy-9-fluoreneone may be used to prepare a monomer of formula (1) by first reacting 3-hydroxy-9-flureonone with dimethylsulfate in the presence of lithium hydroxide to produce 3-methoxy-9-fluorenone, which upon reaction with phenylmagnesium bromide produces 3-methoxy-9-phenyl-9H-fluoren-9-ol. Reaction of the later with acetyl chloride produces 9-chloro-3-methoxy-9-phenyl-9H-fluorene, and subsequent substitution reaction with phenyl lithium produces 3-methoxy-9,9-diphenyl-9H-fluorene. Finally, deprotection of the methoxy group affords the desired monomer 9,9-diphenyl-9H-fluoren-3-ol.

Polymeric reaction products of the invention may be homopolymers or copolymers, and comprise as polymerized units one or more monomers of formula (1) described above. Preferably, the present polymeric reaction products are copolymers, and more preferably, are copolymers comprising as polymerized units one or more tetraaryl methane monomers of formula (1) and one or more monomers selected from formulae (2) and (3):

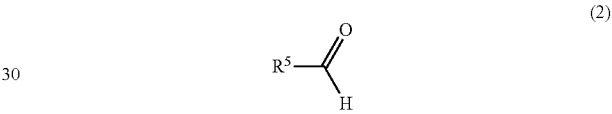

wherein $R^5$ is selected from H, optionally substituted $C_{1-60}$ aliphatic moiety, and optionally substituted $C_{5-60}$ aryl moiety; $Ar^5$ is an optionally substituted $C_{5-60}$ aryl moiety; each $R^6$ is independently chosen from H, optionally substituted $C_{1-60}$ aliphatic moiety, and optionally substituted $C_{5-60}$ aryl moiety; and X is a chosen from OH, $C_{1-2}$ alkoxy group or a halogen. In the context of formulae (2) and (3), a "substituted" aliphatic moiety or aryl moiety refers to any aliphatic moiety or aryl moiety having one or more of its hydrogens replaced with one or more substituents selected from $C_{1-20}$ alkyl, $C_{2-20}$ alkenyl, $C_{7-30}$ aralkyl, or $C_{6-20}$ aryl; and preferably from $C_{1-10}$ alkyl, $C_{2-12}$ alkenyl, $C_{7-30}$ aralkyl, or $C_{6-20}$ aryl. Preferably, $R^5$ is selected from H, optionally substituted $C_{1-60}$ aliphatic moiety, optionally substituted $C_{6-60}$ carbocyclic aryl moiety, and optionally substituted $C_{4-60}$ heteroaryl moiety; and more preferably from H, optionally substituted $C_{1-30}$ aliphatic moiety, and optionally substituted $C_{6-30}$ carbocyclic aryl moiety. Each $R^6$ is preferably selected from H, optionally substituted $C_{1-60}$ aliphatic moiety, optionally substituted $C_{6-60}$ carbocyclic aryl moiety, and optionally substituted $C_{4-60}$ heteroaryl moiety; and more preferably from H, optionally substituted $C_{1-30}$ aliphatic moiety, and optionally substituted $C_{6-30}$ carbocyclic aryl moiety. $Ar^5$ is preferably an optionally substituted $C_{6-60}$ carbocyclic aryl moiety, more preferably an optionally substituted $C_{6-30}$ carbocyclic aryl moiety, and most preferably is chosen from $C_6H_4$, $C_{10}H_6$, $C_{14}H_8$, $C_{12}H_8$, $C_{13}H_8$, $C_{16}H_8$, $C_{18}H_{10}$, and $C_{24}H_{10}$. Preferred monomers of formula (2) include, without limitation: formaldehyde (or its equivalent, paraformaldehyde), benzaldehyde, naphthaldehyde, anthraldehyde, phenanthrenecarboxaldehyde, pyrenecarboxaldehyde, fluorenecarboxaldehyde, and biphenylcarboxaldehyde. Preferred monomers of formula (3) include, 1,4-phenylenedimethanol, 1,4-bis(methoxymethyl)benzene, and 1,4-bis(chloromethyl)benzene. In a further preferred embodiment, the present polymeric reaction product comprises as polymerized units one or more monomers of formula (1) described above, one or more monomers of formulae (2) or (3) as described above, and optionally one or more monomers of the formula $Ar^6$, wherein $Ar^6$ represents an optionally substituted aryl moiety. Any of the aryl moieties described above for $Ar^1$, $Ar^2$, $Ar^3$ and $Ar^4$ may suitably be used for $Ar^6$. Preferably, $Ar^6$ is an optionally substituted $C_{6-40}$ aryl moiety, more preferably an optionally substituted $C_{6-40}$ carbocyclic aryl moiety, and even more preferably an unsubstituted $C_{6-30}$ carbocyclic aryl moiety. Any of the substituents described above for $Ar^1$, $Ar^2$, $Ar^3$, and $Ar^4$, as well as hydroxyl, may suitably be used as the substituents for $Ar^6$. More preferably, $Ar^6$ is chosen from phenol, hydroxynaphthalene, anthracene, hydroxyanthracene, phenanthrene, hydroxyphenanthrene, acenaphthalene, pyrene, 1-pyrenol, tetracene, triphenylene, tetraphene, benzo[f]tetraphene, benzo[m]tetraphene, benzo[k]tetraphene, pentacene, perylene, benzo[a]pyrene, benzo[e]pyrene, benzo[ghi]perylene, coronene, fluorene, and hydroxyfluorene, each of which may optionally be substituted. When $Ar^6$ has <3 fused aromatic rings, it is preferred that $Ar^6$ be substituted with hydroxyl. In general, the ratio of the total amount of aromatic monomers of formula (1) to the amount of monomer of formula (2) or (3) is from 1:1 to 1.5:1, preferably from 1.1:1 to 1.5, and more preferably from 1.1:1 to 1.35:1. Alternatively, the monomer of formula (2) may be used in excess relative to the total amount of the total amount of aromatic monomers of formula (1).

Preferred polymers of the invention are those comprising the repeat unit of formula (4)

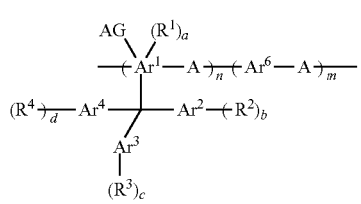

(4)

wherein AG, $Ar^1$, $Ar^2$, $Ar^3$, $Ar^4$, $R^1$, $R^2$, $R^3$, $R^4$, a, b, c and d are as defined above for formula (1); A is chosen from —CH($R^5$)—, —C($R^6$)$_2$—$Ar^5$—C($R^6$)$_2$—, or mixtures thereof; $Ar^y$, $Ar^6$, $R^5$, and $R^6$ are as described above; n and m each represent the number of repeat units in the polymer; n is an integer from 1 to 500; and m is an integer from 0 to 500. Preferably, n=2 to 500, more preferably n=2 to 300, yet more preferably n=2 to 250 and even more preferably n=2 to 100. Preferably, m=0 to 300, more preferably 1 to 300, and even more preferably 1 to 100. It is preferred that A is chosen from —CH($R^5$)—. The polymers of the invention are particularly suitable for use in forming underlayers in a variety of electronic device manufacturing processes.

Polymers of the invention may be prepared by procedures known in the art. One suitable procedure is to react one or more monomers of formula (1) with one or more monomers of formulae (2) or (3), and optionally one or more monomers of the formula $Ar^6$, in a suitable solvent in the presence of an acid, such as pTSA, with heating. Such polymers may be used as is, or may be further purified. Preferably, the polymers are further purified before use. Suitable polymer purification procedures are well-known to those skilled in the art. In general, the present polymers have a molecular weight in the range of 900 to 100,000, and preferably from 900 to 10000. The present polymers may have any suitable polydispersity, such as from 1 to 10, and preferably from 1 to 5.

A suitable composition useful for forming an underlayer comprises one or more of the polymers (aromatic resins) described above, organic solvent, and optionally one or more additives chosen from curing agents and surfactants. It will be appreciated by those skilled in the art that other additives may suitably be used in the present compositions. Compositions of the invention may be prepared by combining the polymer, solvent, and any optional additives in any order. Typically, the amount of the present polymer in these compositions is from 2 to 20 wt %, and preferably from 3 to 15 wt %.

Any solvent may be used, provided that a sufficient amount of the polymeric reaction product is soluble in the solvent, or solvent mixture, used. Such solvents include, but are not limited to, aromatic hydrocarbons, alcohols, lactones, esters, glycols, and glycol ethers. Mixtures of organic solvents may be used. Exemplary organic solvents include, without limitation, toluene, xylene, mesitylene, 2-methyl-1-butanol, 4-methyl-2-pentanol, methyl isobutyl carbinol, gamma-butyrolactone, ethyl lactate, methyl 2-hydroxyisobutyrate, propylene glycol methyl ether acetate, propylene glycol methyl ether, and cyclohexanone. It will be appreciated by those skilled in the art that the concentration of the aromatic resin reaction products in the solvent may be varied across a wide range and that the thickness of any film deposited by a spin-on technique depends on the concentration of the reaction products in the solvent.

Optionally, the present underlayer compositions may further comprise one or more curing agents to aid in the curing of the deposited polymeric reaction product film. A curing agent is any component which causes curing of the polymer on the surface of a substrate. Preferred curing agents are acids and thermal acid generators. Suitable acids include, but are not limited to: arylsulfonic acids such as p-toluenesulfonic acid; alkyl sulfonic acids such as methanesulfonic acid, ethanesulfonic acid, and propanesulfonic acid; perfluoroalkylsulfonic acids such as trifluoromethanesulfonic acid; and perfluoroarylsulfonic acids. A thermal acid generator is any compound which liberates acid upon exposure to heat. Thermal acid generators are well-known in the art and are generally commercially available, such as from King Industries, Norwalk, Conn. Exemplary thermal acid generators include, without limitation, amine blocked strong acids, such as amine blocked sulfonic acids such as amine blocked dodecylbenzenesulfonic acid. It will also be appreciated by those skilled in the art that certain photoacid generators are able to liberate acid upon heating and may function as thermal acid generators. The amount of such curing agents useful in the present compositions is well-known to those skilled in the art and is typically from 0 to 10 wt %, and preferably from 0 to 3 wt %.

The present underlayer compositions may optionally include one or more surface leveling agents (or surfactants). While any suitable surfactant may be used, such surfactants are typically non-ionic. Exemplary non-ionic surfactants are those containing an alkyleneoxy linkage, such as ethyleneoxy, propyleneoxy, or a combination of ethyleneoxy and propyleneoxy linkages. The amount of such surfactants useful in the present compositions is well-known to those skilled in the art, and typically is in the range of 0 to 5 wt %.

The present polymeric reaction products are useful in the manufacture of various electronic devices, such as in a process of forming a patterned layer comprising disposing a layer of the underlayer composition described above on a substrate; removing organic solvent to form a polymeric underlayer; disposing a layer of a photoresist on the polymeric underlayer; exposing the photoresist layer to actinic radiation through a mask; developing the exposed photoresist layer to form a resist pattern; and transferring the pattern to the polymeric underlayer to expose portions of the substrate.

The present compositions may be disposed on an electronic device substrate by any suitable means, such as spin-coating, slot-die coating, doctor blading, curtain coating, roller coating, spray coating, dip coating, and the like. Spin-coating is preferred. In a typical spin-coating method, the present compositions are applied to a substrate which is spinning at a rate of 500 to 4000 rpm for a period of 15-90 sec. to obtain a desired layer of the aromatic resin reaction product on the substrate. It will be appreciated by those skilled in the art that the height of the polymeric reaction product layer (polymeric underlayer) may be adjusted by changing the spin speed.

A wide variety of electronic device substrates may be used in the present invention, such as: packaging substrates such as multichip modules; flat panel display substrates; integrated circuit substrates; substrates for light emitting diodes (LEDs) including organic light emitting diodes (OLEDs); semiconductor wafers; polycrystalline silicon substrates; and the like. Such substrates are typically composed of one or more of silicon, polysilicon, silicon oxide, silicon nitride, silicon oxynitride, silicon germanium, gallium arsenide, aluminum, sapphire, tungsten, titanium, titanium-tungsten, nickel, copper, and gold. Suitable substrates may be in the form of wafers such as those used in the manufacture of integrated circuits, optical sensors, flat panel displays, integrated optical circuits, and LEDs. As used herein, the term "semiconductor wafer" is intended to encompass "an electronic device substrate," "a semiconductor substrate," "a semiconductor device," and various packages for various levels of interconnection, including a single-chip wafer, multiple-chip wafer, packages for various levels, or other assemblies requiring solder connections. Such substrates may be any suitable size, such as wafers having a diameter of 200 mm to 300 mm. As used herein, the term "semiconductor substrate" includes any substrate having one or more semiconductor layers or structures which include active or operable portions of semiconductor devices. A semiconductor device refers to a semiconductor substrate upon which at least one microelectronic device has been or is being batch fabricated.

After being deposited on the substrate, the polymeric (reaction product) underlayer is optionally baked at a relatively low temperature to remove any solvent and other relatively volatile components from the underlayer. Typically, the substrate is baked at a temperature of ≤150° C., preferably from 60 to 125° C., and more preferably from 90 to 115° C. The baking time is typically from 10 sec. to 10 min., preferably from 30 sec. to 5 min., and more preferably from 6 to 90 sec. When the substrate is a wafer, such baking step may be performed by heating the wafer on a hot plate.

The polymeric underlayer is then sufficiently cured such that the film does not intermix with a subsequently applied organic layer, such as a photoresist or other organic layer disposed directly on the underlayer. The polymeric underlayer may be cured in an oxygen-containing atmosphere, such as air, or in an inert atmosphere, such as nitrogen and under conditions, such as heating, sufficient to provide a cured aromatic resin underlayer. Such conditions are sufficient to cure the film such that it does not intermix with a subsequently applied organic layer, such as a photoresist layer, while still maintaining the desired antireflective properties (n and k values) and etch selectivity of the underlayer film. This curing step is conducted preferably on a hot plate-style apparatus, though oven curing may be used to obtain equivalent results. Typically, such curing is performed by heating the polymeric reaction product layer at a curing temperature of ≥150° C., preferably from 150 to 450° C., and more preferably from 200 to 450° C. It is more preferred that the curing temperature is ≥250° C., and even more preferably from 250 to 450° C. The curing temperature selected should be sufficient to cure the polymeric underlayer. When a thermal acid generator is used, the curing temperature should be sufficient for the thermal acid generator to liberate acid to aid in curing of the polymeric underlayer. The curing time may be from 10 sec. to 10 min., preferably from 30 sec. to 5 min., more preferably from 45 sec. to 5 min., and yet more preferably from 45 to 90 sec. The choice of final curing temperature depends mainly upon the desired curing rate, with higher curing temperatures requiring shorter curing times.

The initial baking step may not be necessary if the curing step is conducted in such a way that rapid evolution of the solvents and curing by-products is not allowed to disrupt the underlayer film quality. For example, a ramped bake beginning at relatively low temperatures and then gradually increasing to the range of 200 to 325° C. can give acceptable results. It can be preferable in some cases to have a two-stage curing process, with the first stage being a lower bake temperature of less than 200° C., and the second stage being a higher bake temperature preferably between 200 and 400° C. Two stage curing processes facilitate uniform filling and planarization of pre-existing substrate surface topography, for example filling of trenches and vias.

After curing of the polymeric underlayer, one or more processing layers, such as photoresists, silicon-containing layers, hardmask layers, bottom antireflective coating (or BARC) layers, and the like, may be disposed on the cured underlayer. For example, a photoresist may be disposed, such as by spin coating, directly on the surface of the cured underlayer. A wide variety of photoresists may be suitably used, such as those used in 193 nm lithography, such as those sold under the EPIC™ brand available from Dow Electronic Materials (Marlborough, Mass.). Suitable photoresists may be either positive tone development or negative tone development resists. Following coating on the cured underlayer, the photoresist layer is then imaged (exposed) using patterned actinic radiation, and the exposed photoresist layer is then developed using the appropriate developer to provide a patterned photoresist layer. The pattern is next transferred from the photoresist layer to the underlayer by an appropriate etching technique. Typically, the photoresist is also removed during such etching step. Next, the pattern is transferred to the substrate and the cured underlayer is removed by appropriate etching techniques known in the art, such as by plasma etching. Following patterning of the substrate, the cured underlayer is removed using conventional techniques. The electronic device substrate is then processed according to conventional means.

Alternatively, the cured underlayer may be used as the bottom layer of a multilayer resist process. In such a process, a layer of the polymeric reaction product is disposed on a substrate and cured as described above. Next, one or more middle layers are disposed on the cured underlayer. For example, a silicon-containing layer or a hardmask layer is disposed directly on the cured underlayer. Exemplary silicon-containing layers include a silicon-BARC, which may be spin coated on the underlayer followed by curing, or an inorganic silicon layer such as SiON or $SiO_2$ which may be deposited on the underlayer by chemical vapor deposition (CVD). Any suitable hardmask may be used and may be deposited on the underlayer by any suitable technique, and cured as appropriate. Optionally, an organic BARC layer may be disposed directly on the silicon-containing layer or hardmask layer, and appropriately cured. Next, a photoresist, such as those used in 193 nm lithography, is disposed directly on the silicon-containing layer (in a trilayer process) or directly on the organic BARC layer (in a quadlayer process). The photoresist layer is then imaged (exposed) using patterned actinic radiation, and the exposed photoresist layer is then developed using the appropriate developer to provide a patterned photoresist layer. The pattern is next transferred from the photoresist layer to the layer directly below it, by appropriate etching techniques known in the art, such as by plasma etching, resulting in a patterned silicon-containing layer in a trilayer process and a patterned organic BARC layer in a quadlayer process. If a quadlayer process is used, the pattern is next transferred from the organic BARC layer to the silicon-containing layer or hardmask layer using appropriate pattern transfer techniques, such as plasma etching. After the silicon-containing layer or hardmask layer is patterned, the cured underlayer is then patterned using appropriate etching techniques, such as $O_2$ or $CF_4$ plasma. Any remaining patterned photoresist and organic BARC layers are removed during etching of the cured underlayer. Next, the pattern is then transferred to the substrate, such as by appropriate etching techniques, which also removes any remaining silicon-containing layer or hardmask layer, followed by removal of any remaining patterned cured underlayer to provide a patterned substrate.

Polymeric reaction products of the invention may also be used in a self-aligned double patterning process. In such a process, a layer of a polymeric reaction product described above is disposed on a substrate, such as by spin-coating. Any remaining organic solvent is removed and the polymeric (aromatic resin) layer is cured to form an aromatic resin underlayer. A layer of a suitable photoresist is then disposed on the cured aromatic resin underlayer, such as by spin coating. The photoresist layer is then imaged (exposed) using patterned actinic radiation, and the exposed photoresist layer is then developed using the appropriate developer to provide a patterned photoresist layer. The pattern is next transferred from the photoresist layer to the aromatic resin underlayer by an appropriate etching technique to expose portions of the substrate. Typically, the photoresist is also removed during such etching step. Next, a conformal silicon-containing layer is disposed over the patterned polymeric reaction product layer and exposed portions of the substrate. Such silicon-containing layer is typically an inorganic silicon layer such as SiON or $SiO_2$ which is conventionally deposited by CVD. Such conformal coatings result in a silicon-containing layer on the exposed portions of the substrate surface as well as over the underlayer pattern, that is, such silicon-containing layer substantially covers the sides and top of the underlayer pattern. Next, the silicon-containing layer is partially etched (trimmed) to expose a top surface of the patterned aromatic resin underlayer and a portion of the substrate. Following this partial etching step, the pattern on the substrate comprises a plurality of features, each feature comprising a line or post of the aromatic resin underlayer with the silicon-containing layer directly adjacent to the sides of each aromatic resin underlayer feature. Next, the aromatic resin underlayer is removed, such as by etching, to expose the substrate surface that was under the aromatic resin underlayer pattern, and providing a patterned silicon-containing layer on the substrate surface, where such patterned silicon-containing layer is doubled (that is, twice as many lines and/or posts) as compared to the patterned aromatic resin underlayer.

An advantage of the present polymers is that they have reduced oxygen content as compared to polymers formed from conventional tetraaryl methane monomers. Thus, cured underfills formed from the present polymeric reaction products have improved etch selectivity as compared to underfills formed from conventional tetraaryl methane monomers. The present tetraaryl methane monomers have relatively high carbon content, and relatively low H content. The present polymeric reaction products have relatively high thermal stability (≥400° C.), relatively high modulus, and relatively high film density, which are critical properties are critical for overcoming etch selectivity issues and to prevent pattern deformation, such as occurs with conventional high-carbon content materials used as underlayers. The present polymers also have good planarizing properties and are useful in gap-fill applications. Accordingly, the present compositions may be used to deposit a planarizing or gap-fill layer of the present polymers.

EXAMPLE 1

Under nitrogen atmosphere, a solution of 9-fluorenone (18.2 g, 100 mmol) in 150 mL of dry tetrahydrofuran (THF) was dropwise added at 0° C. to 100 mL of a 1M solution of phenylmagnesium bromide solution in THF. At the end of addition, the reaction mixture was stirred at room temperature for 16 hr. The reaction mixture was poured into 100 mL of saturated solution of ammonium chloride. The mixture was extracted twice with diethyl ether. The combined ether solution was dried over $MgSO_4$ and the solvent was removed under reduced pressure to provide 19.5 g (76%) of intermediate (I1). $^1H$ NMR ($CDCl_3$) δ: 7.72=7.73 (m, 2H), 7.27-7.57 (m, 11H). $^{13}C$ NMR ($CDCl_3$) δ: 150.74, 143.5, 139.87, 135.02, 129.38, 128.75, 128.53, 127.51, 125.71, 125.12124.69, 120.619, 120.39.

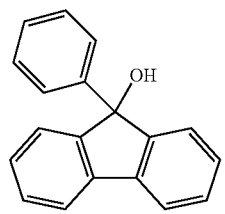

(I1)

EXAMPLE 2

To a solution of intermediate (I1) (7.6 g, 29.5 mmol) and phenol (2.7 g, 28.7 mmol) in 60 mL of 1,2-dichloroethane was added pTSA monohydrate (0.5 g, 2.6 mmol) and the mixture was stirred at 70° C. for 3 hr. The reaction mixture was transferred into a separation funnel and washed once with 50 mL of 0.5% aqueous solution of ammonium bicarbonate, followed by three washes with deionized water (50 mL each). The 1,2-dichloroethane was removed under reduced pressure to produce tetraaryl methane monomer (1-1a) (7.5 g, 85%). $^1$H and $^{13}$C NMR analysis showed that the product consisted of two structural isomers, which were not isolated. The product mixture was used in subsequent reactions.

EXAMPLE 3

To a solution of intermediate (I1) (15 g, 58 mmol) and 2-naphthol (8.3 g, 57.57 mmol) in 100 mL of 1,2-dichloroethane was added pTSA monohydrate (0.8 g, 4.22 mmol) and the mixture was stirred at 70° C. for 4 hr. The reaction mixture was transferred into a separation funnel and washed once with 100 mL of 0.5% aqueous solution of ammonium bicarbonate, followed by two washes with deionized water (100 mL each). The 1,2-dichloroethane was removed under reduced pressure to produce tetraaryl methane monomer (1-1b) (20.3 g, 91%). $^1$H and $^{13}$C NMR analysis showed that the product consisted of structural isomers, which were not isolated. The product mixture was used in subsequent reactions.

EXAMPLE 4

To a solution made of intermediate (I1) (8 g, 31.0 mmol) and pyrene-1-ol (6.5 g, 30 mmol) in 100 mL of 1,2-dichloroethane was added pTSA monohydrate (0.3 g, 1.57 mmol) and the mixture was stirred at 70° C. for 4 hr. The reaction mixture was cooled to room temperature and insoluble material was removed by filtration. The filtrate was washed once with 100 mL of 0.5% aqueous solution of ammonium bicarbonate, followed by two washes with deionized water (100 mL each). The 1,2-dichloroethane was removed under reduced pressure to produce tetraaryl methane monomer (1-1d) (6.9, 49%). $^1$H and $^{13}$C NMR analysis showed that the product consisted of structural isomers, which were not isolated. The product mixture was used in subsequent reactions.

EXAMPLE 5

The procedure of Example 1 is repeated except that the phenylmagnesium bromide is replaced with β-naphthylmagnesium bromide to provide intermediate (I2).

EXAMPLE 6

The procedure of Example 1 is repeated except that the 9-fluorenone is replaced with anthraquinone and 200 mL of 1M phenylmagnesium bromide is used to provide intermediate (I3).

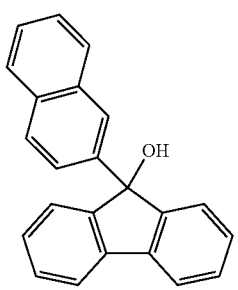

(I2)

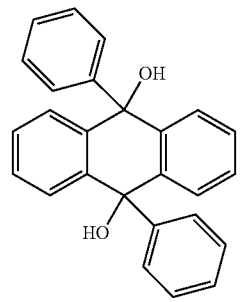

(I3)

EXAMPLE 7

The procedure of Example 2 is repeated except that intermediate (I1) is replaced with triphenylmethanol (intermediate (I4)) to provide tetraaryl monomer (1a).

EXAMPLE 8

The procedure of Example 3 is repeated except that intermediate (I1) is replaced with α-(4-pyridyl)benzhydrol (intermediate (I5)) to provide tetraaryl monomer (1m).

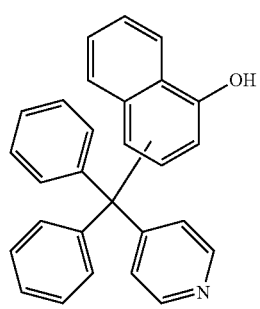

(1m)

EXAMPLE 9

The procedure of Example 3 is repeated except that the intermediate (I1) is replaced intermediate (I2) to provide tetraaryl monomer (1-1g).

EXAMPLE 10

The procedure of Example 3 is repeated except that the intermediate (I1) is replaced intermediate (I3) and 105 mmol of 2-naphthol is used to provide tetraaryl monomer (1-2b).

EXAMPLE 11

The procedure of Example 3 is repeated except that the intermediate (I1) is replaced intermediate (I3) and 60 mmol of pyrene-1-ol is used to provide tetraaryl monomer (1-2c).

EXAMPLE 12

To a solution of tetraaryl monomer (1-1a) (5.0 g, 14.51 mmol) from Example 2 and paraformaldehyde (0.6 g, 19.8 mmol) in 15 mL propyleneglycol monomethylether acetate (PGMEA) was added pTSA monohydrate (0.15 g, 0.8 mmol). The reaction mixture was stirred under nitrogen atmosphere at 120° C. for 16 hr. The mixture was cooled to room temperature and poured slowly into methanol (200 mL) to precipitate polymer A. Polymer A was filtered off and washed with methanol. The resulting crude polymer was suspended in 30 mL of MeOH and stirred for 2 hr. at room temperature. The polymer was filtered and dried. The polymer was analyzed by GPC which showed $M_w=1940$ and $M_w/M_n=1.3$.

EXAMPLE 13

The procedure of Example 12 was repeated except that 13.0 g (33.8 mmol) of tetraaryl monomer (1-1b) from Example 3, 1.1 g (36.3 mmol) of paraformaldehyde, and 0.32 g (1.68 mmol) of pTSA in 45 mL of PGMEA were used to prepare polymer B. Polymer B was analyzed by GPC which showed $M_w=1400$ and $M_w/M_n=1.3$.

EXAMPLE 14

The procedure of Example 12 was repeated except that 8.0 g (16.85 mmol) of tetraaryl monomer (1-1d) from Example 4; 0.6 g (20.2 mmol) of paraformaldehyde, and 0.16 g (0.84 mmol) of pTSA in 25 mL of PGMEA were used to produce polymer C. Polymer C was analyzed by GPC which showed $M_w=2630$ and $M_w/M_n=1.8$.

EXAMPLE 15

The procedure of Example 14 was repeated except that 7.35 g (15.3 mmol) of tetraaryl monomer (1-1d) from Example 4; 2.4 g (15.36 mmol) of 2-napthaldehyde, and 0.5 g (5.2 mmol) of methanesulfonic acid in 30 mL of PGMEA were used to produce polymer D. Polymer D was analyzed by GPC which showed $M_w=1200$ and $M_w/M_n=1.3$.

EXAMPLE 16

The procedure of Example 12 is repeated except that paraformaldehyde is replaced with pyrenecarboxaldehyde and pTSA is replaced with methanesulfonic acid to produce polymer E.

EXAMPLE 17

The procedure of Example 15 is repeated except that 2-napthaldehyde is replaced with 4-biphenylcarboxaldehyde to produce polymer F.

EXAMPLE 18

The procedure of example 12 is repeated except that tetraaryl monomer (1-1a) is replaced with tetraaryl monomer (1a) to produce polymer G.

EXAMPLE 19

The procedure of example 12 is repeated except that tetraaryl monomer (1-1a) is replaced with tetraaryl monomer (1m) to produce polymer H.

EXAMPLE 20

The procedure of example 13 is repeated except that paraformaldehyde is replaced with phenanthrenecarboxaldehyde to provide polymer I.

EXAMPLE 21

The procedure of Example 15 is repeated except that tetraaryl monomer (1-1d) is replaced with tetraaryl monomer (1-2c) to produce polymer J.

EXAMPLE 22

The thermal stability of polymers of the invention were determined using thermal gravimetric analysis (TGA). Polymers A and B were individually formulated in propyleneglycol monomethylether acetate (PGMEA) at 10 wt % solids. Polymer C was formulated in cyclohexanone at 10% solids. Each solution was then filtered through 0.2 μm poly(tetrafluoroethylene) (PTFE) syringe filter, coated on a silicon wafer at 1500 rpm and baked at 100° C. for 60 sec. to remove the solvent and further cured at 400° C. for 60 sec. The cured films were scraped off the wafers and analyzed by TGA. The results are reported in Table 1, and show that the present polymeric reaction products have good thermal stability.

TABLE 1

|  | Under Air | | | Under Nitrogen | | |
| --- | --- | --- | --- | --- | --- | --- |
| Polymer | Weight loss at 400° C. | Temperature (° C.) at 5% weight loss | Temperature (° C.) at 10% weight loss | Weight loss at 400° C. | Temperature (° C.) at 5% weight loss | Temperature (° C.) at 10% weight loss |
| A | 6.8% | 386 | 419 | 3.6% | 423 | 475 |
| B | 3.6% | 418 | 459 | 2.9% | 426 | 467 |
| C | 3.6% | 397 | 441 | 3.6% | 416 | 452 |

EXAMPLE 23

Polymers A and B were individually formulated in PGMEA at 10 wt % solids. Polymers C and D were formulated in cyclohexanone at 10% solid. Comparative polymers C1 (polycondensation product of 1-naphthol and formaldehyde, from Gun Ei Chemical, $M_w=6066$, and $M_n=2362$) and C2 (polycondensation product of 6,6'-(9H-fluorene-9,9-diyl)bis(naphthalen-2-ol) and 1,4-bis(methoxymethyl)benzene, from Gun Ei Chemical) were formulated in PGMEA at 10 wt % solids. Each solution was then filtered through 0.2 μm PTFE syringe filter, coated on a silicon wafer at 1500 rpm and baked at 100° C. for 60 sec. to remove the solvent and further cured at 400° C. for 60 sec. Each cured film was evaluated for etch selectivity using $O_2$ and $CF_4$ plasmas. The etch rate was calculated from the etch time and the difference in thickness of the film before and after etching. Etching tests were carried out using PLASMA-THERM™ RIE790 from Plasma-Therm Co. The etching conditions are summarized in Table 2 and the etching results are reported in Table 3.

TABLE 2

| Polymer | Gas | |
|---|---|---|
| | O₂ | CF₄ |
| Flow (sscm) | 60 | 50 |
| Power (W) | 700 | 500 |
| Pressure (mTorr) | 10 | 10 |

TABLE 3

| Polymer | O₂ etch (Å/sec.) | CF₄ etch (Å/sec.) |
|---|---|---|
| A | 30.3 | 3.0 |
| B | 28.6 | 4.1 |
| C | 26.0 | 2.0 |
| D | 27.1 | 5.1 |
| C1 | 32.9 | 4.2 |
| C2 | 34.2 | — |

What is claimed is:

1. A polymeric reaction product comprising polymerized units of one or more tetraaryl monomers of formula (1) and one or more monomers chosen from formulae (2) and (3):

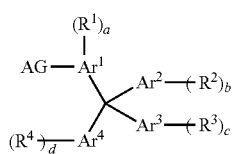

(1)

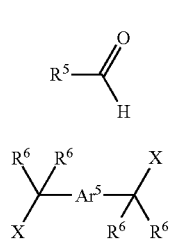

(2)

(3)

wherein AG represents an activating group chosen from OR, NR₂, and SR; $Ar^1$, $Ar^2$, $Ar^3$ and $Ar^4$ independently represent an aryl moiety; R is independently H, an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; $R^1$, $R^2$, $R^3$, and $R^4$ are independently an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; a is an integer from 0 to 4; b, c, and d are independently integers from 0 to 5; $R^5$ is selected from the group consisting of H, optionally substituted $C_{1-60}$ aliphatic moiety, and optionally substituted $C_{5-60}$ aryl moiety; $Ar^5$ is an optionally substituted $C_{5-60}$ aryl moiety, each $R^6$ is independently chosen from H, optionally substituted $C_{1-60}$ aliphatic moiety, and optionally substituted $C_{5-60}$ aryl moiety, and X is OH, $C_{1-2}$ alkoxy group or a halogen; wherein at least one of $Ar^1$, $Ar^2$, $Ar^3$ and $Ar^4$ is an aryl moiety having 2 or more fused aromatic rings, and wherein none of $Ar^1$, $Ar^2$, $Ar^3$ and $Ar^4$ are taken together along with the carbon to which they are attached to form a 5 or 6-membered fused alicyclic ring.

2. The polymeric reaction product of claim 1 wherein AG is OR.

3. The polymeric reaction product of claim 1 wherein $Ar^1$, $Ar^2$, $Ar^3$ and $Ar^4$ are independently chosen from phenyl, biphenyl, naphthalenyl, anthracenyl, phenanthrenyl, pyrenyl, tetracenyl, triphenylenyl, tetraphenyl, benzo[f]tetraphenyl, benzo[m]tetraphenyl, benzo[k]tetraphenyl, pentacenyl, perylenyl, benzo[a]pyrenyl, benzo[e]pyrenyl, benzo[ghi]perylenyl, coronenyl, quinolonyl, 7,8-benzoquinolinyl, fluorenyl, chrysenyl, triphenylenyl, and 12H-dibenzo[b,h]fluorenyl.

4. A composition comprising the polymeric reaction product of claim 1, an organic solvent, and optionally one or more additives chosen from curing agents and surfactants.

5. The composition of claim 4 wherein the curing agent is an acid or a thermal acid generator.

6. A method of forming a patterned layer comprising disposing a layer of the composition of claim 4 on a substrate; removing organic solvent to form a polymeric underlayer; disposing a layer of a photoresist on the polymeric underlayer; exposing the photoresist layer to actinic radiation through a mask; developing the exposed photoresist layer to form a resist pattern; and transferring the pattern to the polymeric underlayer to expose portions of the substrate.

7. A tetraaryl methane monomer having the formula (1)

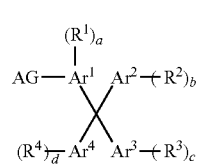

(1)

wherein AG represents an activating group chosen from OR, NR₂, and SR; $Ar^1$, $Ar^2$, $Ar^3$ and $Ar^4$ independently represent an aryl moiety; R is independently H, an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; $R^1$, $R^2$, $R^3$, and $R^4$ are independently an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; a is an integer from 0 to 4; and b, c, and d are independently integers from 0 to 5; wherein at least one of $Ar^1$, $Ar^2$, $Ar^3$ and $Ar^4$ is an aryl moiety having 2 or more fused aromatic rings, and wherein none of $Ar^1$, $Ar^2$, $Ar^3$ and $Ar^4$ are taken together along with the carbon to which they are attached to form a 5 or 6-membered fused alicyclic ring; wherein when AG is OR, R is not a H atom, and wherein when AG is NR₂ and one R is a H atom, the other R is not a $C_6$ aryl moiety.

8. A tetraaryl monomer having the general formula (1-2):

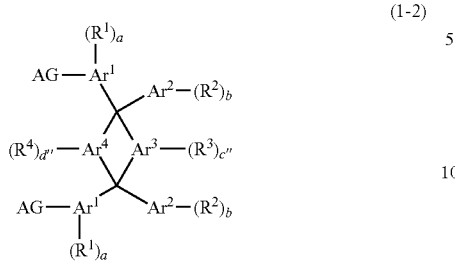

AG represents an activating group chosen from OR, NR2, and SR; $Ar^1$, $Ar^2$, $Ar^3$ and $Ar^4$ independently represent an aryl moiety; R is independently H, an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; $R^1$, $R^2$, $R^3$, and $R^4$ are independently an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; any 2 of $Ar^1$, $Ar^2$, $Ar^3$ and $Ar^4$ may be taken together along with the carbon to which they are attached to form a 5 or 6-membered fused alicyclic ring; a is an integer from 0 to 4; b is an integer from 0 to 5; and c" and d" are independently integers from 0 to 4; wherein when AG is $NR_2$, the two groups are nor aryl moieties simultaneously.

9. A polymeric reaction product comprising polymerized units of one or more tetraaryl monomers of claim 8 and one or more monomers chosen from formulae (2) and (3):

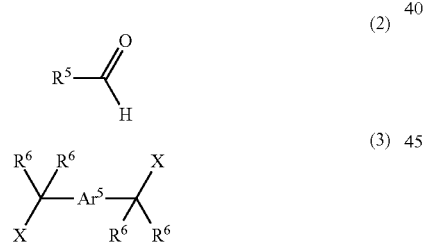

wherein $R^5$ is selected from the group consisting of H, optionally substituted $C_{1-60}$ aliphatic moiety, and optionally substituted $C_{5-60}$ aryl moiety; $Ar^5$ is an optionally substituted $C_{5-60}$ aryl moiety; each $R^6$ is independently selected from the group consisting of H, optionally substituted $C_{1-60}$ aliphatic moiety, and optionally substituted $C_{5-60}$ aryl moiety; and X is OH, $C_{1-2}$ alkoxy group or a halogen.

10. A composition comprising the polymeric reaction product of claim 9, an organic solvent, and optionally one or more additives chosen from curing agents and surfactants.

11. A method of forming a patterned layer comprising disposing a layer of the composition of claim 10 on a substrate; removing organic solvent to form a polymeric underlayer; disposing a layer of a photoresist on the polymeric underlayer; exposing the photoresist layer to actinic radiation through a mask; developing the exposed photoresist layer to form a resist pattern; and transferring the pattern to the polymeric underlayer to expose portions of the substrate.

12. A polymer comprising a repeat unit of formula (4)

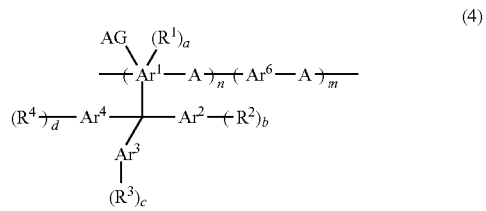

wherein AG represents an activating group chosen from OR, $NR_2$, and SR; $Ar^1$, $Ar^2$, $Ar^3$ and $Ar^4$ independently represent an aryl moiety; R is independently H, an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; $R^1$, $R^2$, $R^3$, and $R^4$ are independently an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; any 2 of $Ar^1$, $Ar^2$, $Ar^3$ and $Ar^4$ may be taken together along with the carbon to which they are attached to form a 5 or 6-membered fused alicyclic ring; a is an integer from 0 to 4; and b, c, and d are independently integers from 0 to 5; wherein at least one of $Ar^1$, $Ar^2$, $Ar^3$ and $Ar^4$ is an aryl moiety having 2 or more fused aromatic rings when none of $Ar^1$, $Ar^2$, $Ar^3$ and $Ar^4$ are joined to form a 5 or 6-membered fused alicyclic ring; A is chosen from —$CH(R^5)$—, —$C(R^6)_2$—$Ar^5$—$C(R^6)_2$—, or mixtures thereof; $R^5$ is selected from the group consisting of H, optionally substituted $C_{1-60}$ aliphatic moiety, and optionally substituted $C_{5-60}$ aryl moiety; $Ar^5$ is an optionally substituted $C_{5-40}$ aryl moiety; $Ar^6$ is an optionally substituted $C_{5-60}$ aryl moiety; each $R^6$ is independently chosen from H, optionally substituted $C_{1-60}$ aliphatic moiety, and optionally substituted $C_{5-60}$ aryl moiety; n and m each represent the number of repeat units in the polymer; n is an integer from 1 to 500; and m is an integer from 1 to 300.

13. The polymer of claim 12 wherein $Ar^1$, $Ar^2$, $Ar^3$ and $Ar^4$ are independently chosen from phenyl, biphenyl, naphthalenyl, anthracenyl, phenanthrenyl, pyrenyl, tetracenyl, triphenylenyl, tetraphenyl, benzo[f]tetraphenyl, benzo[m]tetraphenyl, benzo[k]tetraphenyl, pentacenyl, perylenyl, benzo[a]pyrenyl, benzo[e]pyrenyl, benzo[ghi]perylenyl, coronenyl, quinolonyl, 7,8-benzoquinolinyl, fluorenyl, chrysenyl, triphenylenyl, and 12H-dibenzo[b,h]fluorenyl.

14. The polymer of claim 12 wherein A is —$CH(R^5)$—.

15. The polymer of claim 12 wherein $Ar^5$ is an optionally substituted $C_{6-60}$ carbocyclic aryl moiety.

16. A composition comprising the polymer of claim 12, an organic solvent, and optionally one or more additives chosen from curing agents and surfactants.

17. A method of forming a patterned layer comprising disposing a layer of the composition of claim 16 on a substrate; removing organic solvent to form a polymeric underlayer; disposing a layer of a photoresist on the polymeric underlayer; exposing the photoresist layer to actinic radiation through a mask; developing the exposed photoresist layer to form a resist pattern; and transferring the pattern to the polymeric underlayer to expose portions of the substrate.

18. The method of claim 17 further comprising disposing a silicon-containing layer or a hardmask layer directly on the polymeric underlayer, and disposing the photoresist layer directly on the silicon-containing layer or hardmask layer.

19. A polymeric reaction product comprising polymerized units of one or more tetraaryl monomers of formula (1)

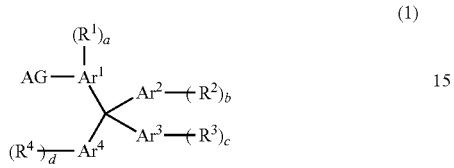

wherein AG represents an activating group chosen from OR, $NR_2$, and SR; $Ar^1$, $Ar^2$, $Ar^3$ and $Ar^4$ independently represent an aryl moiety; R is independently H, an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; $R^1$, $R^2$, $R^3$, and $R^4$ are independently an optionally substituted $C_{1-30}$ alkyl, an optionally substituted $C_{2-30}$ alkenyl moiety, an optionally substituted $C_{2-30}$ alkynyl moiety, an optionally substituted $C_{7-30}$ aralkyl moiety, or an optionally substituted $C_{6-20}$ aryl moiety; a is an integer from 0 to 4; and b, c, and d are independently integers from 0 to 5, wherein at least one of $Ar^1$, $Ar^2$, $Ar^3$ and $Ar^4$ is an aryl moiety having 2 or more fused aromatic rings, and wherein none of $Ar^1$, $Ar^2$, $Ar^3$ and $Ar^4$ are taken together along with the carbon to which they are attached to form a 5 or 6-membered fused alicyclic ring; and formed by heating the one or more tetraaryl monomers in the presence of an acid.

* * * * *